US005693707A

United States Patent [19]
Cheng et al.

[11] Patent Number: 5,693,707
[45] Date of Patent: Dec. 2, 1997

[54] LIQUID ABSORBENT COMPOSITION FOR NONWOVEN BINDER APPLICATIONS

[75] Inventors: John Tze-Chiang Cheng, Allentown; Finn Lennart Marten, Emmaus; Joel Erwin Goldstein, Allentown; Chung-Ling Mao, Emmaus, all of Pa.

[73] Assignee: Air Products and Chemicals, Inc., Allentown, Pa.

[21] Appl. No.: 373,729

[22] Filed: Jan. 17, 1995

Related U.S. Application Data

[63] Continuation-in-part of Ser. No. 308,027, Sep. 16, 1994, abandoned.

[51] Int. Cl.$^6$ .............................. C08L 31/06; C08L 33/08
[52] U.S. Cl. ..................... 524/556; 524/558; 524/560
[58] Field of Search ........................ 524/556, 458, 524/558, 560; 525/329.9, 328.8, 329.5, 329.7, 330.2, 363, 378

[56] References Cited

U.S. PATENT DOCUMENTS

| | | | |
|---|---|---|---|
| 3,865,764 | 2/1975 | Drelich et al. | 260/17 R |
| 4,090,013 | 5/1978 | Ganslaw et al. | 526/15 |
| 4,320,040 | 3/1982 | Fujita et al. | |
| 4,666,983 | 5/1987 | Tsubakimoto et al. | |
| 4,683,274 | 7/1987 | Nakamura et al. | |
| 4,735,987 | 4/1988 | Morita et al. | |
| 4,743,244 | 5/1988 | LeKhac | 525/186 |
| 4,914,170 | 4/1990 | Chang et al. | 526/240 |
| 5,002,986 | 3/1991 | Fujiura et al. | 524/734 |
| 5,118,719 | 6/1992 | Lind | 521/92 |
| 5,192,617 | 3/1993 | Stofko, Jr. | |
| 5,196,456 | 3/1993 | Nguyen et al. | 522/84 |

FOREIGN PATENT DOCUMENTS

| | | |
|---|---|---|
| 0031628 | 7/1981 | European Pat. Off. |
| 0133779 | 3/1985 | European Pat. Off. |

*Primary Examiner*—Jeffery T. Smith
*Attorney, Agent, or Firm*—Michael Leach; William F. Marsh

[57] ABSTRACT

An aqueous polymer composition comprising 10 to 40 wt % of a polymer in water, the polymer consisting essentially of 20–90 wt % $\alpha,\beta$-ethylenically unsaturated carboxylic acid monomer, 10–80 wt % one or more softening monomers, the aqueous composition being adjusted to pH 4–6 with alkali metal hydroxide or alkaline earth metal hydroxide and further containing 0.1 to 3 wt % zirconium crosslinking salt. Such aqueous compositions can be applied to nonwoven and woven substrates to make superabsorbent products.

23 Claims, No Drawings

LIQUID ABSORBENT COMPOSITION FOR NONWOVEN BINDER APPLICATIONS

CROSS-REFERENCE TO RELATED APPLICATIONS

This application is continuation-in-part of application Ser. No. 08/308,027 filed on 16 Sep. 1994, now abandoned which is incorporated by reference.

TECHNICAL FIELD

The invention relates to certain polymers characterized by their ability to absorb a large amount of water, which polymers are generally referred to as superabsorbing polymers.

BACKGROUND OF THE INVENTION

Superabsorbing polymers find application in the medical industry, the food industry and agriculture and, further, are used in many consumer products. Superabsorbing polymers are of great interest in personal hygiene products such as diapers, incontinent pads, and feminine care products. Normally, they are used in their usual commercial granular or powdered form, in mixtures with various cellulosic fibers. Those fibers, for example, wood pulp or modified cellulose fibers, when used alone, have certain shortcomings in that the fluid is held mainly in the interstices between individual fibers and can be readily squeezed out under pressure, and the mechanical strength of the fibers is significantly reduced when wet. Because of that, cellulosic fibers by themselves are not ideal absorbent materials for such applications. The addition of superabsorbing polymers to the pulp improves the retention of fluid under pressure and gives a blend with increased absorptive capacity.

Superabsorbing polymers swell to a large degree in contact with water, but do not fully dissolve. They are usually prepared by either one of two methods, namely, crosslinking water-soluble polymers to make them water insoluble, while allowing them to retain their ability to swell in water; or modifying water-insoluble polymers by introducing hydrophilic groups to cause swelling in contact with water. The first method is the one most commonly used to prepare superabsorbing polymers. The crosslink density is of critical importance since too little crosslinking produces a soft, loose gel, which still is quite water soluble, while too much crosslinking reduces polymer swelling and thus its ability to absorb water.

The commercial absorbent materials are primarily based on the powdered form of sodium acrylate/acrylic acid polymers or copolymers. One of the shortcomings for the powder material is that the hard granular particles require nonwoven manufacturers to subject their web to another operation to add the powder to the composite for personal care applications. As another shortcoming, the prior art commercial superabsorbing polymers normally do not have sufficient tack to adhere to the cellulosic fibers with which they are blended. As a result, they tend to separate from the cellulosic fibers and migrate within the pad or sift out of the pad during handling; i.e., these are problems of uneven distribution and shifting of particles due to lack of adhesion to the substrate. Obviously, it would be desirable to fix the superabsorbing polymer in place in the pad so that the polymer does not migrate.

WO 90/08806 discloses superabsorbing copolymers of vinyl alcohol which are made by alcoholysis, in the presence of a small amount of an alkali metal alkoxide or hydroxide, of a precursor copolymer VAc/X/Y, where VAc stands for vinyl acetate; X is a dialkyl ester of one of specified ethylenically unsaturated dicarboxylic acids; and Y is a copolymerizable ethylenically unsaturated monocarboxylic acid.

U.S. Pat. No. 4,320,040 discloses a method for producing a hydrophilic gel comprising polymerizing acrylic acid and/or methacrylic acid, or a neutralized product thereof, in the presence of polyvinyl alcohol to obtain a polymer which is subjected to heat treatment, wherein the polymerization is carried out in an aqueous solution having a total concentration of acrylic acid and/or methacrylic acid or its neutralized product and polyvinyl alcohol of 10–60% by weight, the heat treatment temperature being 50° to 150° C. and the weight ratio of polyvinyl alcohol to acrylic acid and/or methacrylic acid or its salt being 5-95:95-5.

U.S. Pat. No. 4,743,244 discloses a polymer composition which is water-absorbent upon curing comprising:

(a) a copolymer containing from about 25 to 75 mole % of at least one $\alpha,\beta$-unsaturated monomer bearing at least one carboxylic acid unit; and (b) a polyether derived from $C_2$ to $C_{10}$ alkylene oxides.

U.S. Pat. No. 4,683,274 discloses a water-absorbent resin produced by subjecting an aqueous solution of an $\alpha,\beta$-unsaturated carboxylic acid and an alkali metal salt thereof to polymerization with a radical polymerization initiator in a petroleum-based hydrocarbon solvent in the presence or absence of a crosslinking agent and, in this polymerization, using a saccharose-fatty acid ester as a protective colloid agent.

U.S. Pat. No. 4,735,987 discloses a method for the manufacture of a high-expansion type absorbent polymer characterized by causing an absorbent polymer which results from the polymerization of a monomer and an alkali salt of acrylic acid to be crosslinked, during azeotropic dehydration thereof, with a crosslinking agent possessing two or more functional groups in the presence of an inorganic substance and the drying of the crosslinked absorbent polymer.

U.S. Pat. No. 4,666,983 discloses an absorbent article obtained by mixing 100 parts by weight of an absorbent resin powder, having a carboxyl group with 0.001 to 10 parts by weight of a crosslinking agent having at least two functional groups capable of reacting with the carboxyl group per molecule and reacting the absorbent resin powder with the crosslinking agent to crosslink the molecular chains existing at least in the vicinity of the surface of the absorbent resin powder.

U.S. Pat. No. 5,192,617 discloses cross-linked polymeric compositions capable of forming continuous matrices for liquid absorbent, semi-interpenetrating polymer networks.

SUMMARY OF THE INVENTION

The present invention provides an aqueous polymer composition comprising 10 to 40 wt % of a carboxylate-containing polymer in water which has been adjusted with an alkali metal hydroxide or alkaline earth metal hydroxide to pH 4 to 6. The polymer consists essentially of 20–90 wt % $\alpha,\beta$-ethylenically unsaturated carboxylic acid monomer and at least one softening monomer in an amount effective to yield a polymer having a Tg<140° C. To afford a liquid absorbent composition, the aqueous composition would further contain a divalent or trivalent metal crosslinking agent.

As an advantage of the invention, the carboxylate-containing polymer may be applied to the absorbent core substrate, namely loose cellulosic fibers or a nonwoven or woven web, in liquid form, i.e., as an aqueous solution or dispersion, in a single step operation, thus resulting in a more uniform and consistent layer of polymer on the fibers or web. In addition, the polymer remains in place on the substrate.

As another embodiment of the invention there are also provided superabsorbent fibers comprising fibers containing a sufficient amount of the superabsorbing polymer to provide fibers having enhanced absorbent properties.

The polymer not only possesses sufficient tack to adhere to the fibers of the nonwoven web but also has sufficient adhesive strength to act as a binder for the nonwoven web. The addition of the crosslinking agent for the carboxylate functionality affords the superabsorbent property.

Therefore, as an embodiment of the invention there is also provided a nonwoven web of fibers bonded together with a sufficient amount of the superabsorbing polymer composition to provide a self-sustaining superabsorbent web.

As another embodiment of the invention there is also provided a nonwoven web of fibers bonded together with a sufficient amount of a binder polymer to provide a self-sustaining web and also a sufficient amount of the superabsorbing polymer composition to provide a superabsorbent web.

As still a further embodiment of the invention, the alkali or alkaline earth metal hydroxide, pH adjusted aqueous polymer composition is further adjusted to pH 8.5 to 10 with a fugitive base to provide enhanced solution stability.

DETAILED DESCRIPTION OF THE INVENTION

The liquid absorbent polymer composition of the invention comprises an aqueous medium of 10 to 40 wt % solids of a polymer prepared by aqueous solution or emulsion polymerization of the monomers in the presence of a stabilizing system comprising at least one polyvinyl alcohol (PVOH) or at least one surfactant, or mixture thereof. The polymer consists essentially of an α,β-ethylenically unsaturated carboxylic acid monomer and one or more softening monomers such as, for example, vinyl alkanoates, dialkyl maleates or fumarates, and alkyl acrylates. When PVOH is used in the stabilizing system, the monomers become grafted onto or complexed with the PVOH backbone.

Suitable carboxylic acid monomers which compose 20 to 90 wt %, preferably 40 to 80 wt %, of the polymer may be any one or more of the α,β-ethylenically unsaturated mono- or dicarboxylic acids and acid anhydrides, such as acrylic acid, methacrylic acid, crotonic acid, maleic acid/anhydride, itaconic acid, fumaric acid and the like. The preferred carboxylic acid monomer for use in the present invention is acrylic acid.

The polymer also contains one or more softening monomers to provide the polymer and resulting absorbent product with drape and flexibility. Such monomers are used in amounts sufficient to yield a polymer having a Tg<140° C., preferably a Tg ranging from −20° to +120° C. The Tg is determined on a polymer which has been neutralized with aqueous sodium hydroxide to a pH of 5–5.5, i.e., about 75% neutralized.

"Softening monomers" are those copolymerizable monomers whose homopolymer exhibits a Tg<35° C. Such softening monomers would include vinyl alkanoates, alkyl acrylates and methacrylates and mono- and diesters of dicarboxylic acid monomers.

Suitable vinyl alkanoates includes any of the $C_1$–$C_{12}$ esters of vinyl alcohol, such as vinyl formate, vinyl propionate, vinyl butyrate, vinyl versatate, and preferably vinyl acetate. These monomers may compose 10–60 wt %, preferably 20–40 wt %, of the polymer. Vinyl acetate homopolymer has a Tg of −32° C.

As to softening monomers which are mono- or diesters of dicarboxylic acid monomers and may compose 5–30 wt %, preferably 5–20 wt %, of the polymer, they may be a mono- or dialkyl maleate or fumarate such as any mono- or diester of maleic acid or fumaric acid with a $C_1$–$C_{16}$ alkanol, preferably a $C_4$–$C_8$ alkanol, i.e., octyl alcohol, isooctyl alcohol, butyl alcohol, isobutyl alcohol, amyl alcohol, tridecyl alcohol and the like. The preferred comonomer is dioctyl maleate.

Alkyl (meth)acrylates which may be softening monomers are those esters of acrylic or methacrylic acid with a $C_2$–$C_8$ alkanol such as butyl acrylate, butyl methacrylate, hexyl acrylate, preferably 2-ethylhexyl acrylate, and the like. The homopolymer of 2-ethylhexyl acrylate, for example, has a Tg of −70° C. Suitable alkyl (meth)acrylates may be compose 10–50 wt %, preferably 20–40 wt %, of the polymer. Again, the combination and amounts of softening monomers must be such as to afford, in combination with carboxylic acid monomer and any other comonomers, a polymer having a Tg<140° C.

The monomers can be polymerized in an aqueous medium in the presence of at least one PVOH which is 80–99 mole % hydrolyzed and has a degree of polymerization (DPn) ranging from 150 to 1500, preferably 200 to 800. It is preferred to use a PVOH which is partially (87–89 mole %) hydrolyzed with a DPn of 200 to 800. The PVOH is used at 1–10 wt %, preferably 2–8 wt %, based on copolymerizable monomers. Of course, it is possible to use a combination of PVOH's. It is believed that the PVOH acts as the site, or backbone, for the graft polymerization or complexation of the comonomers.

In addition to, or in place of, the PVOH composing the stabilizing system for the aqueous polymerization reaction, emulsifying agents, or surfactants, can be used. Emulsifying agents composing the stabilizing system which can be used in the polymerization recipe include those ionic and nonionic surfactants well known in the aqueous polymerization art, preferably the anionic types. The concentration range of the total amount of the emulsifying agents useful is from 0.5 to 10%, based on total emulsion.

The aqueous composition of the carboxylic acid-containing polymer contains about 10 to 40 wt %, preferably 15 to 30 wt %, solids. It is adjusted to a pH of about 4–6 using an alkali metal hydroxide, such as sodium hydroxide or potassium hydroxide, or an alkaline earth metal hydroxide, such as calcium hydroxide. It is preferred to use sodium or potassium hydroxide. (Obviously, a metal alkoxide can be use in place of the metal hydroxide.) It is also preferred to adjust the aqueous solution to about pH 5 to 5.5.

It is preferred that polymers for making the superabsorbent product yield an aqueous solution or dispersion having a sufficiently low viscosity so it can be applied to the web as a spray.

To effect crosslinking of the polymer through its carboxylate functionality and thus create a superabsorbing polymer on the fibrous web, a sufficient amount of crosslinking compound is added to the aqueous polymer composition. Although any well known di- or trivalent crosslinking salt, such as zirconium, zinc or chromium salts, may be used, zirconium salts such as zirconium acetate, zirconium carbonate, or ammonium or potassium zirconium carbonate are preferred. The most preferred material is ammonium zirconium carbonate. Such zirconium crosslinking salts are available from Magnesium Elektron, Inc. The carboxylate crosslinking salts are included in the aqueous composition at 0.1 to 3 wt %, preferably 0.5 to 1.3 wt %, based on polymer solids.

Any free radical generating source, such as peroxides and persulfates, may be used to initiate the polymerization of the monomers and carry out the polymerization reaction. Combination-type systems employing both reducing agents and oxidizing agents well known in the art, i.e., redox systems, can also be used. However, it is preferred to use an alkali metal persulfate such as potassium persulfate.

When reference is made to incremental addition, whether of vinyl acetate, any comonomer or free radical source, substantially uniform additions, both with respect to quantity and time, and intermittent additions are contemplated. Such additions are often referred to as "delay" additions.

Suitable aqueous polymer compositions can be prepared by polymerizing the monomers in the presence of an aqueous solution of PVOH. Substantially all of the PVOH in water and a portion of the softening monomer(s), e.g., vinyl acetate, and acrylic acid are initially charged to the polymerization vessel. Most advantageously, at least about 10 to 30 wt % and preferably at least about 15 wt % of the total vinyl acetate to be polymerized is initially charged to the reactor. Similarly, at least about 10 to 50 wt % and preferably at least about 20 wt % of the total acrylic acid to be polymerized is initially charged to the reactor. The aqueous composition is then adjusted to pH 4–5 with alkali metal or alkaline earth metal hydroxide solution. The remaining amounts of the vinyl acetate and acrylic acid are desirably delay additions. The entire amount of the softening monomers may desirably be added initially (upfront).

The polymerization reacton is performed at temperature ranging from 55° to 75° C., preferably about 75° C., when using persulfate initiators.

More specifically, an aqueous solution containing the PVOH is initially prepared. At least 10 wt % of the carboxylate-containing monomer, is then added and the solution is adjusted with an alkali metal hydroxide or alkaline earth metal hydroxide to a pH of about 4.5. At least 10 wt % of the vinyl acetate and all of the dialkyl maleate or fumarate is then added to the aqueous medium. Polymerization is initiated by the addition of the free radical source. After the initiation a delay feed of the remaining carboxylic acid containing monomer, the remaining vinyl acetate and additional free radical source are added as delays. The polymerization reaction is generally continued until the residual vinyl acetate and acrylic acid monomer content is below about 0.5%.

The resulting aqueous polymer composition is treated with an aqueous solution of alkali or alkaline earth metal hydroxide or alkoxide until the pH is about 4–6, preferably 5–5.5. The zirconium crosslinking salt, such as Bacote 20 ammonium zirconium carbonate, is added to the stirred polymer solution or dispersion.

In order to improve the long-term stability of the aqueous polymer solution or dispersion containing a crosslinking zirconium salt, a fugitive base is used to adjust the pH to 8.5 to 10, preferably 8.7 to 9.3. Suitable fugitive bases would include ammonia and any amine that is sufficiently volatile so as to migrate from the aqueous polymer composition upon heating and curing so as to allow the zirconium salt to coordinate with the carboxylic acid groups to effect crosslinking. In addition to the preferred ammonia as aqueous ammonium hydroxide, other suitable volatile amines include methylamine and dimethylamine. The fugitive base should be added to the composition before the zirconium salt.

The aqueous absorbent polymer composition can be applied, for example by spraying, onto loose fibers, preferably cellulosic fibers, to produce a superabsorbent product. The amount of the absorbent polymer applied to the fibers is that amount sufficient to provide enhanced absorbent properties to the fibers and may range from 5 to 50 wt %, preferably 10 to 25 wt %, of the fibers. The produced superabsorbent fibers may be used in many applications including as the fluff in diapers. Examples of the fibers to be used in making the superabsorbent product are the natural cellulose fibers such as wood pulp, cotton and hemp and the synthetic cellulose fibers such as rayon and regenerated cellulose.

The aqueous absorbent polymer composition can also be sprayed, foam coated, printed or dip saturated onto a nonwoven or woven web to afford a superabsorbent product. The nonwoven web can be bonded with polymer binders well known in the art, such as vinyl acetate/ethylene/N-methylolacrylamide (VAE-NMA) copolymers, self-crosslinking acrylics and styrene-butadienes, and the liquid absorbent composition applied thereto, or the polymer composition itself may have sufficient adhesive qualities (tack and wet and dry strength) to use it as both the nonwoven binder and the absorbent material.

Thus, various copolymer binders known in the art can be used to prepare nonwoven products, or fabrics, by a variety of methods known in the art which, in general, involve the impregnation of a loosely assembled mass of fibers with the binder emulsion, followed by a moderate heating to dry the mass. This moderate heating also serves to cure the binder by forming a crosslinked interpolymer. Before the binder is applied, it is, of course, mixed with a suitable catalyst for the crosslinking monomer. For example, an acid catalyst such as mineral acids, e.g., hydrogen chloride, or organic acids, e.g., oxalic acid, or acid salts such ammonium chloride, are suitably used as known in the art. The amount of catalyst is generally from 0.5 to 2% of the total polymer.

The starting fiber layer or mass can be formed by any one of the conventional techniques for depositing or arranging fibers in a web or layer. These techniques include carding, garnetting, air-laying, wet laying and the like. Individual webs or thin layers formed by one or more of these techniques can also be laminated to provide a thicker layer for conversion into a fabric. Typically, the fibers extend in a plurality of diverse directions in general alignment with the major plane of the fabric, overlapping, intersecting and supporting one another to form an open, porous structure.

Examples of the fibers to be used in the starting layer are the natural cellulose fibers such as wood pulp, cotton and hemp and the synthetic cellulose fibers such as rayon, and regenerated cellulose. Often the fiber starting layer contains at least 50% cellulose fibers, whether they be natural or synthetic, or a combination thereof. Often the fibers in the starting layer may comprise natural fiber such as wool, jute; artificial fibers such as cellulose acetate; synthetic fibers such as polyamides, nylon, polyesters, acrylics, polyolefins, i.e., polyethylene, polyvinyl chloride, polyurethane, and the like, alone or in combination with one another.

The fibrous starting layer is subjected to at least one of several types of bonding operations to anchor the individual fibers together to form a self-sustaining web. Some of the better known methods of bonding are overall impregnation or printing the web with intermittent or continuous straight or wavy lines for areas of binder extending generally transversely or diagonally across the web and additionally, if desired, along the web.

Where the absorbent polymer composition is used also as the binder polymer, it is applied to the fibrous starting web in an amount which is sufficient to form a self-sustaining web and provide enhanced absorbent properties upon crosslinking and suitably ranges from about 3 to about 100 wt % or more of the starting web, preferably about 10 to 50 wt % of the starting web. The impregnated web is then dried and cured. The nonwoven products are suitably dried by passing them through air ovens or the like and then through a curing oven. Typical conditions of time and temperature are well known in the art. Where a separate binder polymer is used to bond the nonwoven web, the absorbent polymer is applied to the bonded web in an amount sufficient to provide enhanced absorbent properties to the web and may range from 5 to 50 wt %, preferably 10 to 25 wt %, of the web.

In addition to applying the aqueous polymer composition comprising the absorbent polymer and metal crosslinking compound to the nonwoven web, the polymer in aqueous medium can be applied followed by the application of the crosslinking metal compound in an aqueous medium, preferably with drying of the absorbent polymer-containing web prior to application of the crosslinking metal compound.

The resulting web will be able to absorb many times its weight of water. The finished web could be used in sanitary products, such as diapers and feminine hygiene products, meat trays, fuel filters, seed strips, agricultural crop cover, and other applications where superabsorbents are used.

EXAMPLE 1

Into a two liter jacketed glass reactor equipped with agitator and reflux condenser were charged the following ingredients:

| INITIAL CHARGE (grams) | | |
|---|---|---|
| 1. | Distilled Water | 700 |
| 2. | AIRVOL ® 205 PVOH[a] (20% soln) | 60 |
| 3. | Acrylic Acid | 40 |
| 4. | Vinyl Acetate | 36 |
| 5. | Dioctyl Maleate | 24 |
| 6. | Potassium Persulfate | 2 |
| DELAY FEED (grams) | | |
| 1. | Acrylic Acid | 140 |
| 2. | Vinyl Acetate (Finishing) | 20 |
| 3. | Potassium Persulfate | 2 |

[a]87–89 mole % hydrolyzed; DPn = 500–600

The 20% aqueous solution of AIRVOL 205 PVOH was added to the distilled water followed by the addition of the acrylic acid. The pH of this aqueous solution was adjusted to about 4.5 with 50% aqueous sodium hydroxide before charging it into the reactor. The vinyl acetate and dioctyl maleate were added under agitation of 300 rpm. The reactor was purged with nitrogen and a small stream of nitrogen was maintained during the polymerization reaction. The reaction was thermally initiated at 65° C. by adding the potassium persulfate. The polymerization temperature was maintained at about 70° C.

One-half hour after the initiation, the delay feed of acrylic acid was started at a rate of 105 g/hr for 2 hours. At the middle of the acrylic acid delay, 1.5 g of potassium persulfate in 20 g water was added followed by the addition of 1.5 g potassium persulfate in 20 g of water and the 20 g vinyl acetate at the end of the acrylic acid delay. The reaction was continued for an additional 3.5 hours at 70° C. A typical aqueous superabsorbent dispersion prepared by this procedure had the following properties:

| PROPERTIES | | |
|---|---|---|
| 1. | Total Solids (%) | 22.6 |
| 2. | Brookfield Viscosity (cps) | 4300 |
| 3. | pH | 4.3 |
| 4. | Acrylic Acid (free monomer) (%) | 0.0 |
| 5. | Vinyl Acetate (free monomer) (%) | 0.02 |
| 6. | Particle Size Distribution | |
| | Dn | 0.1150 µm |
| | Ds | 0.1900 µm |
| | Dw | 0.3570 µm |
| | Polydispersity | 3.104 |
| 7. | Intrinsic Viscosity[a] (dl/g) | 1.01 |

[a]In THF solvent with HCl addition for complete dissolution.

The polymer composition based on ingredients charged was 66.2 wt % acrylic acid, 20.6 wt % vinyl acetate, 8.8 wt % dioctyl maleate, and 4.4 wt % PVOH. This aqueous solution was then treated with a 10% aqueous sodium hydroxide solution until the pH was 5. Bacote 20 ammonium zirconium carbonate (1% active solids on solids) was then added to the stirred solution.

EXAMPLE 2

In this example the procedure of Example 1 was followed with the following exceptions:

| INITIAL CHARGE (grams) | | |
|---|---|---|
| 1. | Distilled Water | 1400 |
| 2. | Aerosol A-102[a] (31% active) | 20.8 |
| 3. | Acrylic Acid | 50 |
| 4. | 2-Ethylhexyl Acrylate | 50 |
| 5. | Dioctyl Maleate | 50 |
| 6. | Potassium Persulfate[b] | 0.7 |
| DELAY FEED (grams) | | |
| 1. | Acrylic Acid | 50 |

[a]Disodium ethoxylated alcohol half ester of sulfosuccinic acid.
[b]Dissolved in 50 g water; added at 60° C.

The initial polymerization temperature was 60° C. Starting one hour after initiation, the acrylic acid was added in one hour. 2.5 hours after the start of the acrylic acid delay, 0.35 g potassium persulfate in 30 ml water was added and the temperature was raised to 70° C. for 2.5 hours more.

This polymer composition was 48.5 wt % acrylic acid, 24.2 wt % 2-ethylhexyl acrylate and 24.2 wt % dioctyl maleate.

| PROPERTIES | | |
|---|---|---|
| 1. | Total Solids (%) | 14.7 |
| 2. | Brookfield Viscosity (cps) | 500 |
| 3. | pH | 3.7 |

EXAMPLE 3

The maximum absorbency capacity of the Example 2 polymer was determined to be 5.94 g 1% aqueous saline solution/g polymer according to the following procedure: 100 grams of the aqueous solution (14.2% solids) was adjusted to pH 6 with 10% aqueous sodium hydroxide. To this dispersion was added 0.71 g Bacote 20 ammonium zirconium carbonate (1% solids on solids) and the resulting aqueous dispersion (0.71 g) was drizzled onto a weighed 7 cm Whatman #1 filter paper disk. The filter paper was dried for 20 minutes at 300° F. (149° C.) and then placed in a sealed plastic bag (prevent humidity absorption) in the controlled temperature and humidity room overnight. The test specimen was then weighed and the amount of polymer present was calculated. The specimen was then sandwiched between two virgin sheets of Whatman #1 filter paper and placed onto the sample holder of a Gravimetric Absorbency Test System (GATS) apparatus (from MK Systems) with a 0.07 psi weight on top to prevent the sample from floating away.

EXAMPLE 4

To 25 g of a 22.6 wt % solids aqueous absorbent polymer composition was added 10% aqueous sodium hydroxide to raise the pH to 5.5. The polymer comprised 65.7 wt % acrylic acid, 21.2 wt % vinyl acetate, 8.8 wt % dioctyl maleate and 4.4 wt % polyvinyl alcohol and was prepared according to the procedure of Example 1. The aqueous composition was then raised to pH 9 with 28% aqueous ammonia followed by the addition of 2.4 g Bacote 20 ammonium zirconium carbonate (1% solids on solids) and mixed for 15 minutes. The aqueous composition was then drizzled onto a pre-weighed 7 cm disc of Whatman #4 filter paper and dried at 300° F. (149° C.) for 20 minutes. The sample was placed in a sealed plastic bag in a controlled temperature and humidity room overnight. The equilibrated sample was sandwiched between 2 blank pieces of Whatman #4 filter paper and placed on the GATS with 0.07 psi weight on it to prevent the sample from floating away. The maximum absorbency capacity was determined to be 15.2 g 1% aqueous saline solution/g polymer, the absorbency under load (AUL) was 14.7 g/g and the rate was 0.18 g/min.

EXAMPLE 5

A pH versus stability ladder of the aqueous polymer solution of Example 1 was performed.

TABLE

| pH | Initial Viscosity | 24 Hour Viscosity |
|---|---|---|
| 5.0 | — | gel |
| 5.5 | — | gel |
| 6.0 | — | gel |
| 7.0 | 39,000 | gel |
| 7.5 | 20,000 | gel |
| 8.0 | 9,790 | 15,740 |
| 8.5 | 4,630 | 4,560 |
| 9.0 | 5,000 | 5,200 |

It can be seen from the Table that a pH of about 8.5 and above provides a product having a relatively stable viscosity over a 24 hour period.

Since the polymer exists as an aqueous solution or dispersion of low viscosity, it can be applied as a liquid as by spraying onto a web to afford a more uniform and consistent layer of superabsorbing polymer that will remain in place.

EXAMPLE 6

This example shows the preparation of an emulsion superabsorbent polymer.

Into a two liter jacketed glass reactor equipped with agitator and reflux condenser were charged the following ingredients:

| INITIAL CHARGE (grams) | | |
|---|---|---|
| 1. | Distilled Water | 400 |
| 2. | Potassium Persulfate* | 5.0 |

*Predissolved and added at 65° C.

The polymerization temperature was maintained at 70° C. and the agitation was 300 rpm. The total polymerization run time was 6 hours. The following delay feed was added to the reactor at a substantially uniform rate over 3 hours. At the end of the delay addition 2 g potassium persulfate was added.

| DELAY FEED* (grams) | | |
|---|---|---|
| 1. | Igepal CO-630 surfactant | 4.6 |
| 2. | Airvol 205 PVOH (10% soln) | 138.7 |
| 3. | Acrylic Acid | 200.0 |
| 4. | Vinyl Acetate | 50.0 |
| 5. | 2-Ethylhexyl Acrylate | 200.0 |

*Components 1–3 were mixed and adjusted to pH 4 with aqueous sodium hydroxide followed by the addition of components 4 and 5.

The resulting emulsion had the following properties:

| PROPERTIES | | |
|---|---|---|
| 1. | Total Solids (%) | 37.5 |
| 2. | Brookfield Viscosity (cps) | 12,200 |
| 3. | pH | 4.2 |
| 4. | Tg | 119° C. |

Using Bacote 20 ammonium zirconium carbonate (1% solids on solids) the maximum absorbency capacity (pH=5) was 15.4 g 1% saline solution/g polymer and the absorbency under load (AUL) was 11.2 g 1% saline solution/g polymer.

STATEMENT OF INDUSTRIAL APPLICATION

The present invention provides an aqueous composition of an absorbent polymer for use in preparing superabsorbent materials such as superabsorbent cellulosic fibers and superabsorbent nonwoven webs.

We claim:

1. An aqueous polymer composition comprising 10 to 40 wt % of a polymer in water, the polymer consisting of 20–90 wt % α,β-ethylenically unsaturated carboxylic acid monomer and at least one softening monomer selected from the group consisting of vinyl alkanoates, monoesters or diesters of maleic acid or fumaric acid with a $C_1$–$C_{16}$ alkanol, esters of acrylic or methacrylic acid with a $C_2$–$C_8$ alkanol and mixtures thereof in a sufficient amount so that the polymer has a Tg of <140° C., the softening monomer having a homopolymer that exhibits a Tg±35° C., the aqueous polymer composition being adjusted to pH 4–6 with alkali metal hydroxide or an alkaline earth metal hydroxide and a divalent or trivalent metal crosslinking compound post-added to the aqueous polymer composition in an amount effective to yield a superabsorbing polymer.

2. The aqueous polymer composition of claim 1 in which the α,β-ethylenically unsaturated carboxylic acid monomer is selected from the group consisting of acrylic acid, methacrylic acid, crotonic acid, maleic acid, itaconic acid, fumaric acid and mixtures thereof.

3. The aqueous polymer composition of claim 1 in which the softening monomers are selected from the group consisting of $C_1$–$C_{12}$ esters of vinyl alcohol, diesters of maleic acid or fumaric acid with a $C_1$–$C_{16}$ alkanol, esters of acrylic or methacrylic acid with a $C_2$–$C_8$ alkanol and mixtures thereof.

4. The aqueous polymer composition of claim 1 in which the polymer consists essentially of 40 to 80 wt % $\alpha,\beta$-ethylenically unsaturated carboxylic acid monomer and has a Tg from $-20°$ to $+120°$ C.

5. The aqueous polymer composition of claim 1 in which the divalent or trivalent metal crosslinking compound is a salt of zirconium, zinc or chromium.

6. An aqueous polymer composition comprising 10 to 40 wt % of a polymer in water, the polymer consisting of 20–90 wt % $\alpha,\beta$-ethylenically unsaturated carboxylic acid monomer selected from the group consisting of acrylic acid, methacrylic acid, crotonic acid, maleic acid, itaconic acid and fumaric acid and mixtures thereof, and one or more softening monomers selected from the group consisting of $C_1$–$C_{12}$ esters of vinyl alcohol, diesters of maleic acid or fumaric acid with a $C_1$–$C_{16}$ alkanol and esters of acrylic or methacrylic acid with a $C_2$–$C_8$ alkanol in a sufficient amount so that the polymer has a Tg<140° C., the softening monomer having a homopolymer that exhibits a Tg $\pm 35°$ C., the aqueous polymer composition being adjusted to pH 4–6 with alkali metal hydroxide or alkaline earth metal hydroxide and 0.1 to 3 wt % zirconium crosslinking salt post-added to the aqueous polymer composition to yield a superabsorbing polymer.

7. The aqueous polymer composition of claim 6 in which the polymer consists essentially of 40 to 80 wt % $\alpha,\beta$-ethylenically unsaturated carboxylic acid monomer and has a Tg from $-20°$ to $+120°$ C.

8. The aqueous polymer composition of claim 7 in which the zirconium salt is selected from the group consisting of zirconium acetate, zirconium carbonate, potassium zirconium carbonate and ammonium zirconium carbonate.

9. An aqueous polymer composition comprising 10 to 40 wt % of a polymer in water, the polymer consisting of 20–90 wt % acrylic acid and one or more softening monomers selected from the group consisting of vinyl acetate, diesters of maleic acid with a $C_4$–$C_8$ alkanol and esters of acrylic or methacrylic acid with a $C_2$–$C_8$ alkanol in a sufficient amount so that the polymer has a Tg<140° C., the softening monomer having a homopolymer that exhibits a Tg$\pm 35°$ C., the aqueous polymer composition being adjusted to pH 4–6 with alkali metal hydroxide and 0.1 to 3 wt % zirconium crosslinking salt selected from the group consisting of zirconium acetate, zirconium carbonate, potassium zirconium carbonate and ammonium zirconium carbonate post-added to the aqueous polymer composition to yield a superabsorbing polymer.

10. The aqueous polymer composition of claim 9 in which the polymer has a Tg of $-20°$ to $+120°$ C.

11. The aqueous polymer composition of claim 10 in which the softening monomers are selected from the group consisting of vinyl acetate, dioctyl maleate, 2-ethylhexyl acrylate and mixtures thereof.

12. The aqueous polymer composition of claim 5 in which the pH is subsequently adjusted to 8.5 to 10 with a fugitive base.

13. The aqueous polymer composition of claim 6 in which the pH is subsequently adjusted to 8.5 to 10 with a fugitive base.

14. The aqueous polymer composition of claim 7 in which the pH is subsequently adjusted to 8.5 to 10 with a fugitive base.

15. The aqueous polymer composition of claim 8 in which the pH is subsequently adjusted to 8.5 to 10 with a fugitive base.

16. The aqueous polymer composition of claim 9 in which the pH is subsequently adjusted to 8.5 to 10 with a fugitive base.

17. The aqueous polymer composition of claim 10 in which the pH is subsequently adjusted to 8.5 to 10 with a fugitive base.

18. The aqueous polymer composition of claim 11 in which the pH is subsequently adjusted to 8.5 to 10 with a fugitive base.

19. A nonwoven product comprising a nonwoven web of fibers bonded together with a polymer binder characterized in that the web is bonded with a sufficient amount of a polymer to both bond the fibers and afford enhanced absorbent properties to the web, the polymer deposited on the web from the aqueous composition of claim 1.

20. A nonwoven product comprising a nonwoven web of fibers bonded together with a polymer binder characterized in that the web also contains a sufficient amount of an absorbent polymer to afford enhanced absorbent properties to the web, the absorbent polymer deposited on the web from the aqueous composition of claim 1.

21. A superabsorbent product comprising cellulosic fibers containing a sufficient amount of an absorbent polymer to provide the fibers with enhanced absorbent properties, the absorbent polymer deposited on the fibers from the aqueous composition of claim 1.

22. A superabsorbent product comprising cellulosic fibers containing a sufficient amount of an absorbent polymer to provide the fibers with enhanced absorbent properties, the absorbent polymer deposited on the fibers from the aqueous composition of claim 6.

23. A superabsorbent product comprising cellulosic fibers containing a sufficient amount of an absorbent polymer to provide the fibers with enhanced absorbent properties, the absorbent polymer deposited on the fibers from the aqueous composition of claim 9.

\* \* \* \* \*